United States Patent [19]

Kubicek

[11] 4,120,944

[45] Oct. 17, 1978

[54] PREPARATION OF CARBONYL SULFIDE AND PRODUCTION OF METHYL MERCAPTAN THEREFROM

[75] Inventor: Donald H. Kubicek, Bartlesville, Okla.

[73] Assignee: Phillips Petroleum Company, Bartlesville, Okla.

[21] Appl. No.: 719,220

[22] Filed: Aug. 31, 1976

[51] Int. Cl.$^2$ .................... C01B 31/26; C07C 149/06
[52] U.S. Cl. ................................. 423/416; 260/609 R
[58] Field of Search ...................... 260/609 A, 609 R; 423/416, 415

[56] References Cited

U.S. PATENT DOCUMENTS

| 3,409,399 | 11/1968 | Bertozzi et al. | 423/416 |
| 3,432,266 | 3/1969 | Garlet et al. | 423/415 |
| 3,488,739 | 1/1970 | Venrooy | 260/609 R |

FOREIGN PATENT DOCUMENTS 635,743  1/1962  Canada ............................. 260/609 A Primary Examiner—Earl C. Thomas

[57] ABSTRACT

Methyl mercaptan is prepared by hydrogenating carbonyl sulfide in the presence of a sulfactive catalyst. The carbonyl sulfide is prepared by reacting carbon dioxide and carbon disulfide in the presence of a supported phosphotungstic acid catalyst.

10 Claims, No Drawings

PREPARATION OF CARBONYL SULFIDE AND PRODUCTION OF METHYL MERCAPTAN THEREFROM

The present invention is directed to the preparation of methyl mercaptan.

It is known that methyl mercaptan can be prepared by reacting methyl alcohol and hydrogen sulfide. This method has the disadvantage that the methyl alcohol is relatively expensive. It is also known that methyl mercaptan can be prepared by reacting carbon disulfide and hydrogen. This method has the disadvantage that hydrogen sulfide is also produced. It is desired to prepare methyl mercaptan from relatively inexpensive feedstocks with no net gain of by-product hydrogen sulfide.

It is an object of this invention to provide a process for producing methyl mercaptan.

It is another object of this invention to provide a process for producing carbonyl sulfide.

Other objects, aspects and advantages of this invention will be readily apparent to those skilled in the art from the reading of the following disclosure.

In accordance with the present invention there is provided a process for preparing methyl mercaptan which comprises contacting under reaction conditions a mixture of carbonyl sulfide and hydrogen with a sulfactive hydrogenation catalyst consisting essentially of a catalytically active combination of at least one Group VIII metal sulfide and at least one group VI metal sulfide on an inorganic oxide support.

In one embodiment of this invention there is provided a process for producing carbonyl sulfide by catalytically reacting carbon dioxide and carbon disulfide by contacting a mixture of carbon dioxide and carbon disulfide with a supported phosphotungstic acid catalyst.

In another embodiment of this invention, there is provided a two-step process for preparing methyl mercaptan comprising first converting carbon dioxide and carbon disulfide to carbonyl sulfide and, second, hydrogenating the carbonyl sulfide to provide methyl mercaptan.

By sulfactive hydrogenation catalyst it is meant the sulfides of Group VI and Group VIII metals, either alone or in combination. For example, the sulfides of cobalt, nickel, molybdenum, iron, tungsten, chromium, platinum, and the like can be used. Generally the catalytic material is incorporated with a support such as activated carbon, alumina, zirconia, thoria, silica and silica-alumina. Combinations of nickel or cobalt with molybdenum are generally among the more preferred of such catalysts. Quite effective catalysts of the foregoing preferred combination but in the oxide form are available commercially. One such catalyst, available commercially, consists essentially of cobalt oxide (about 3-4 weight percent) and molybdenum oxide (about 15-16 weight percent), the remainder being alumina. It is easily sulfided using well-known and conventional sulfiding conditions, conventional techniques and equipment. For example, flowing hydrogen sulfide, alone or mixed with hydrogen at about 350° to 700° F. and a pressure of about atmospheric to 300 psig.

The reaction between hydrogen and carbonyl sulfide is carried out at a temperature in the approximate range of 300° to 600° F. (about 150°-315° C.), preferably from about 375° to about 450° F. (about 190°-230° C.).

Hydrogen is admixed with the carbonyl sulfide in an amount ranging from 3 to 10 moles of hydrogen per mole of carbonyl sulfide. Hydrogen sulfide can also be admixed with the feedstream as a reaction modifier/moderator. If used, the amount will generally be from about 1 to about 10 moles of hydrogen sulfide per mole of carbonyl sulfide.

The reaction between hydrogen and carbonyl sulfide is carried out under a pressure between 0 and 1000 psig (101 and 6995 kPa), preferably from 200 to 700 psig (1480 to 4927 kPa).

The above reaction is carried out under conditions such that the space velocity can be expressed in liquid volumes of carbonyl sulfide per volume of catalyst per hour (LHSV). Broadly, the LHSV can range from 0.01 to 10.

The carbonyl sulfide is prepared by contacting a mixture of carbon dioxide and carbon disulfide with a supported phosphotungstic acid catalyst.

The supported phosphotungstic acid catalyst consists of from 0.1 to 10 weight percent phosphotungstic acid on a suitable support material. The catalyst is conveniently prepared by impregnating a support material with an aqueous solution of phosphotungstic acid sufficient to provide 0.1 to 10 weight percent phosphotungstic acid based on the weight of the finished catalyst. Following impregnation, the water is removed and the catalyst is dried.

Suitable support materials for the phosphotungstic acid are inorganic oxide support materials such as silica, alumina, silica-alumina, magnesia, thoria, titania and the like.

The above reaction between carbon disulfide and carbon dioxide is carried out at a temperature in the approximate range of 400° to 550° F. (204° to 288° C.).

The above reaction is carried out at a pressure in the range of 0 to 500 psig (101 to 3550 kPa). The above reaction is carried out at a gaseous hourly space velocity (GHSV) of about 100 to 10,000, based upon the finished catalyst.

The product methyl mercaptan is used as an intermediate in making agricultural chemicals.

An advantage of the overall process for producing carbonyl sulfide and for producing methyl mercaptan therefrom is that all of the sulfur from the carbon disulfide is incorporated into methyl mercaptan; there is no net gain of hydrogen sulfide.

The following examples illustrate the invention:

EXAMPLE I

Preparation of Carbonyl Sulfide 1.0 gram of phosphotungstic acid ($P_2O_5 \cdot 24WO_3 \cdot xH_2O$) was dissolved in 100 ml distilled water. 50 grams of alumina was added to the solution and thoroughly stirred to insure complete contact of the fresh acid solution with the support. The water was removed and the catalyst was dried at 500° F. (288° C.) for 2 hours in a flowing stream of hydrogen sulfide.

The catalyst was charged to a tubular reaction chamber. The chamber was initially heated to 450° F. (232° C.). A mixture of carbon dioxide and carbon disulfide in a molar ratio of about 2:1 was passed to the reactor at a carbon disulfide feed rate of 1 ml/min. The pressure was maintained at 180 psig (1340 kPa). Samples of the reactor effluent were taken after 60 minutes and 75 minutes of operation and analyzed by gas-liquid chromatography. The results, in terms of area percent of each component, are shown in the following table:

Table I

| Reactor Effluent at 450° F Operating Temperature | | |
|---|---|---|
| Component | 60 minutes | 75 minutes |
| Carbon dioxide | 55.007 | 52.181 |
| Carbonyl sulfide | 43.237 | 45.683 |
| Carbon disulfide | 1.726 | 2.136 |

The temperature of the reactor was then raised to 500° F. (260° C.), the feed mixture continuing as before. Samples were analyzed at 60 and 75 minutes. The results are as follows:

Table II

| Reactor Effluent at 500° F Operating Temperature | | |
|---|---|---|
| Component | 60 minutes | 75 minutes |
| Carbon dioxide | 52.880 | 49.577 |
| Carbonyl sulfide | 46.723 | 49.929 |
| Carbon disulfide | .397 | .494 |

The above results demonstrate a conversion of carbon disulfide to carbonyl sulfide of about 98% at 450° F. and about 99.5% at 500° F.

EXAMPLE II

Preparation of Methyl Mercaptan 50 grams of a commercial catalyst containing 3-4 weight percent cobalt oxide and 15-16 weight percent molybdenum oxide on an alumina support was charged to a tubular reaction chamber and sulfided for 2 hours at 600° F. in flowing hydrogen sulfide.

A mixture of carbonyl sulfide and hydrogen was passed in contact with the sulfided catalyst at the reaction temperatures given in Table III below. Samples of the reactor effluent were taken at the intervals stated below and analyzed by GLC. The carbonyl sulfide feed rate was 0.5 ml/min. and the hydrogen feed rate was 1.6 moles/hour (3.2 g/hr.). Pressure was maintained at 550 spig (3890 kPa). The results are as follows:

Table III

| Reactor Effluent, Area Percent Methyl Mercaptan | | | | | | | |
|---|---|---|---|---|---|---|---|
| Temperature | | Sampling Time (minutes) | | | | | |
| °F | °C | 30 | 45 | 50 | 60 | 75 | 90 |
| 325 | 163 | — | — | — | 0 | 5.46 | — |
| 375 | 191 | — | — | — | 6.91 | 0 | — |
| 425 | 218 | — | — | — | 7.84 | 5.31 | — |
| 450 | 232 | — | — | — | 8.0 | — | — |
| 475 | 246 | — | — | — | 0 | 5.35* | 5.96 |
| 530 | 277 | 5.65 | — | 5.08 | — | — | — |
| 585 | 307 | — | 1.4 | — | — | — | — |

*Contained 13.7 mole percent hydrogen sulfide.

The above data show maximum single pass conversion to methyl mercaptan at 375°-450° F. (191° to 232° C.). Some hydrogen sulfide was produced at 475° F., apparently due to pyrolysis of methyl mercaptan.

Reasonable variations and modifications, which will be apparent to those skilled in the art, can be made in this invention without departing from the spirit and scope thereof.

What is claimed is:

1. A process for the production of methyl mercaptan which comprises contacting at a temperature in the approximate range of 300° to 600° F. and a pressure in the approximate range of 0 to 1000 psig a mixture of carbonyl sulfide and hydrogen with a sulfactive hydrogenation catalyst consisting essentially of a combination of at least one Group VIII sulfide, at least one Group VI sulfide and an inorganic oxide support.

2. The process of claim 1 wherein said carbonyl sulfide is prepared by the reaction of carbon dioxide and carbon disulfide in the presence of a supported phosphotungstic acid catalyst at a temperature in the approximate range of 400° to 550° F. and a pressure in the approximate range of 0-500 psig.

3. The process of claim 2 wherein said carbon dioxide and said carbon disulfide are reacted at a temperature in the approximate range of 400° to 550° F.

4. The process of claim 1 wherein said hydrogenation catalyst prior to sulfidation consists essentially of 70 to 88 weight percent of said support, 2 to 5 weight percent of said Group VIII metal oxide and about 10 to 25 weight percent of said Group VI metal oxide.

5. The process of claim 4 wherein said hydrogenation catalyst prior to sulfidation consists essentially of about 3-4 weight percent of cobalt oxide and about 15-16 weight percent molybdenum oxide, with the remainder being alumina.

6. The process of claim 2 wherein the mole ratio of said carbon dioxide to said carbon disulfide is at least about 1.1:1.

7. The process of claim 1 wherein the mole ratio of said hydrogen to said carbonyl sulfide is at least 3:1.

8. The process according to claim 1 wherein the temperature is in the approximate range of 375° to 450° F. and the pressure is in the range of 200 to 700 psig.

9. A process for the production of carbonyl sulfide which comprises contacting a mixture of carbon dioxide and carbon disulfide with a supported phosphotungstic acid catalyst at a temperature in the approximate range of 400° to 550° F. and a pressure in the approximate range of 0–●psig.

10. The process of claim 9 wherein said catalyst consists of from 0.1 to 10 weight percent phosphotungstic acid, with the remainder being an inorganic oxide support material.

* * * * *

UNITED STATES PATENT AND TRADEMARK OFFICE
CERTIFICATE OF CORRECTION

PATENT NO. : 4,120,944

DATED : October 17, 1978

INVENTOR(S) : Donald H. Kubicek

It is certified that error appears in the above-identified patent and that said Letters Patent are hereby corrected as shown below:

Column 4, line 48, delete "0-·psig" and insert --- 0-500 psig ---.

Signed and Sealed this

Sixth Day of March 1979

[SEAL]

Attest:

RUTH C. MASON
*Attesting Officer*

DONALD W. BANNER
*Commissioner of Patents and Trademarks*